US012766106B2

(12) United States Patent
Kim

(10) Patent No.: US 12,766,106 B2
(45) **Date of Patent: *Oct. 20, 2026**

(54) MICROPARTICLES CONTAINING MOXIDECTIN, AND PREPARATION METHOD THEREFOR

(71) Applicant: INVENTAGE LAB INC., Seongnam-si (KR)

(72) Inventor: Ju Hee Kim, Seongnam-si (KR)

(73) Assignee: INVENTAGE LAB INC. (KR)

( * ) Notice: Subject to any disclaimer, the term of this patent is extended or adjusted under 35 U.S.C. 154(b) by 261 days.

This patent is subject to a terminal disclaimer.

(21) Appl. No.: 18/434,686

(22) Filed: Feb. 6, 2024

(65) Prior Publication Data

US 2024/0238204 A1 Jul. 18, 2024

Related U.S. Application Data

(63) Continuation-in-part of application No. 16/771,196, filed as application No. PCT/KR2018/010324 on Sep. 5, 2018, now Pat. No. 11,931,461.

(30) Foreign Application Priority Data

Sep. 6, 2017 (KR) ........................ 10-2017-0113669
Mar. 20, 2018 (KR) ........................ 10-2018-0031979

(51) Int. Cl.
*A61K 9/16* (2006.01)
*A61K 31/365* (2006.01)

(52) U.S. Cl.
CPC .......... *A61K 9/1647* (2013.01); *A61K 31/365* (2013.01)

(58) Field of Classification Search
CPC ............................ A61K 9/1647; A61K 31/365
See application file for complete search history.

(56) References Cited

U.S. PATENT DOCUMENTS

| | | | | |
|---|---|---|---|---|
| 5,733,566 | A * | 3/1998 | Lewis | A61K 31/7048 424/424 |
| 2010/0226947 | A1* | 9/2010 | Theberge | A61K 8/0208 424/484 |
| 2019/0175507 | A1* | 6/2019 | Cardona | A61K 9/1694 |

FOREIGN PATENT DOCUMENTS

| | | |
|---|---|---|
| CN | 1444946 A | 10/2003 |
| CN | 1698637 A | 11/2005 |

OTHER PUBLICATIONS

Huimin Lin, Application of Modern Separation and Purification Technology in Aquatic Products, Dec. 2015, p. 122, Beijing Ocean Publishing House, Beijing, China, English translation of abstract.

(Continued)

*Primary Examiner* — Jianfeng Song
(74) *Attorney, Agent, or Firm* — STIP Law Group, LLC

(57) ABSTRACT

The present invention relates to microparticles comprising moxidectin and a biodegradable polymer, wherein the microparticles comprising moxidectin have a shape allowing a moxidectin drug to be uniformly distributed in spherical biodegradable polymer particles, and the average particle diameter of the microparticles is 45-130 μm, depending on the type of polymer. The present invention relates to: extended release microparticles capable of continuously maintaining a heartworm disease prevention effect for 3 months to 6 months by administering microparticles comprising moxidectin; and a preparation method therefor. In addition, the present invention is prepared such that the average diameters of the particles have a predetermined micrometer size, and thus reduces a foreign body sensation and pain during administration into an animal through injection, thereby enabling administration through injection to be facilitated.

4 Claims, 6 Drawing Sheets

(56) References Cited

OTHER PUBLICATIONS

Zhiqiang Wang, Dogs and Cats Clinical Medication Manual , Moxidectin, Shanghai Science and Technology, 2009, p. 114, Shanghai Publishing House, Shanghai, China, English translation of abstract.

* cited by examiner

[FIG. 1]
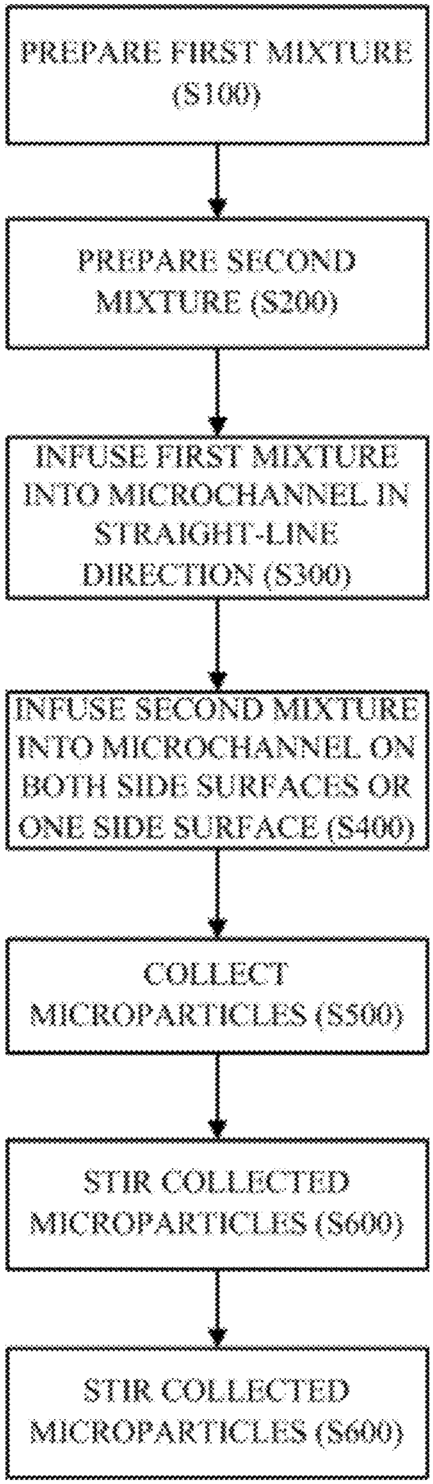

[FIG. 2]
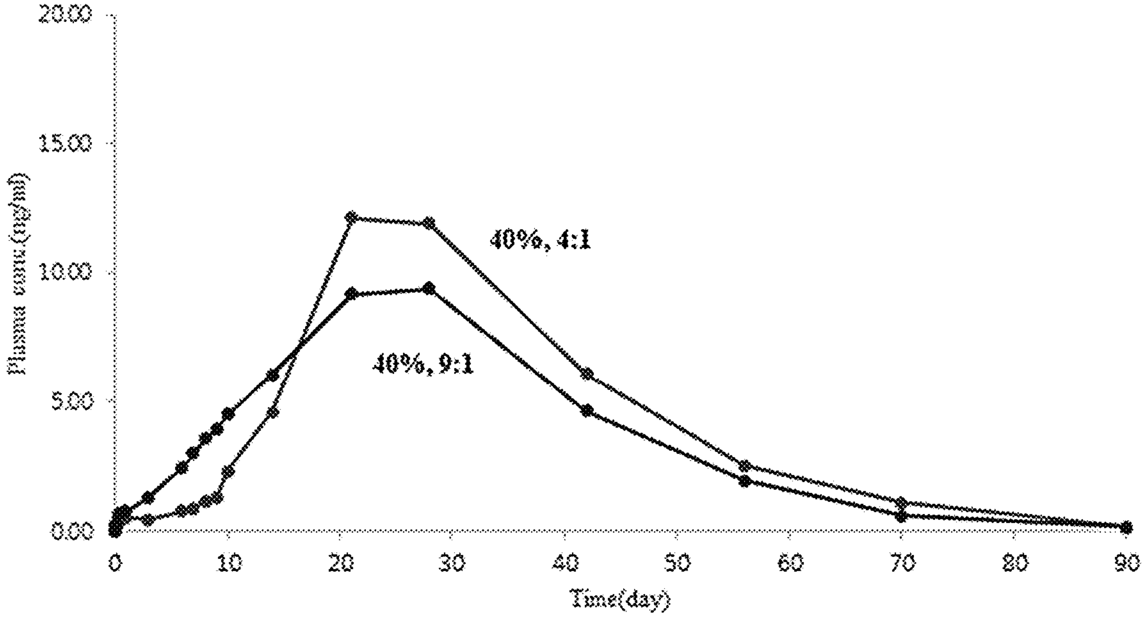
[FIG. 3]
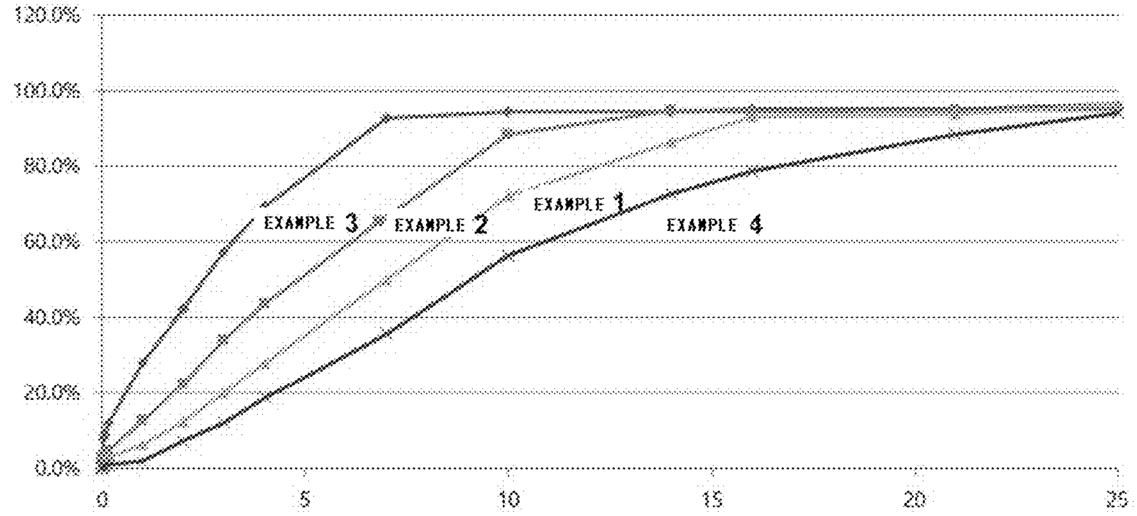

[FIG. 4]
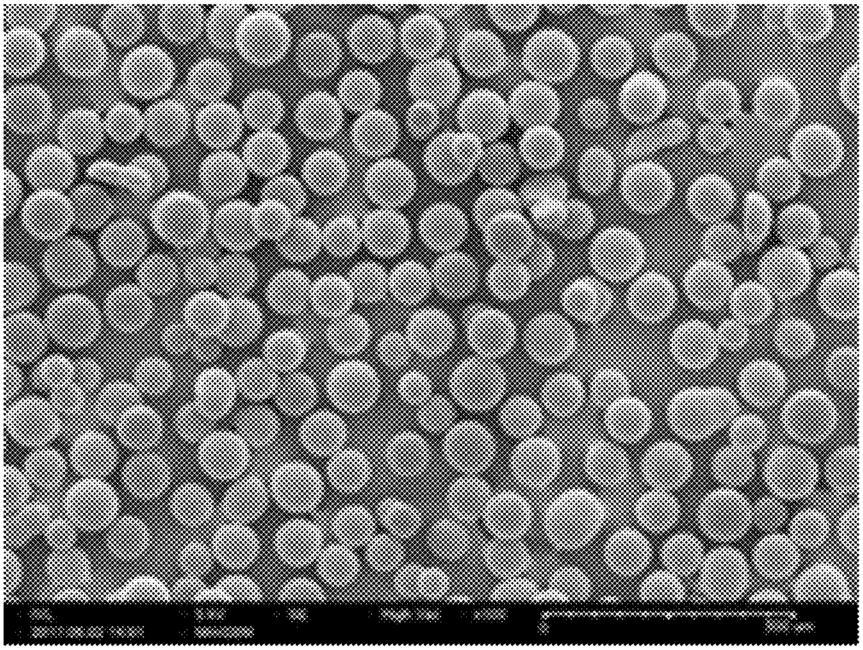
[FIG. 5]
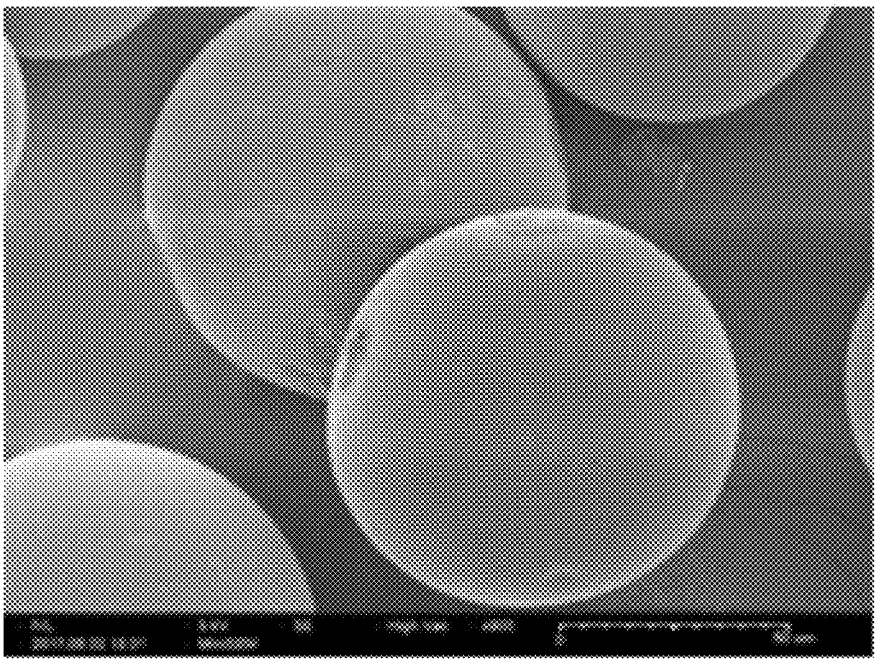

[FIG. 6]
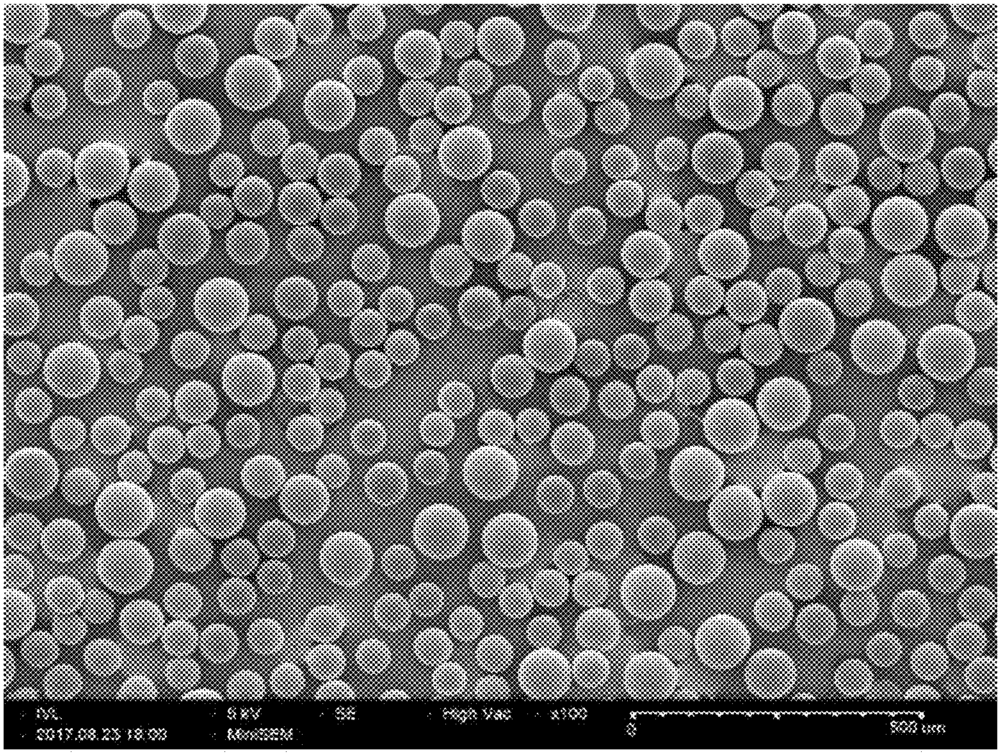

[FIG. 7]
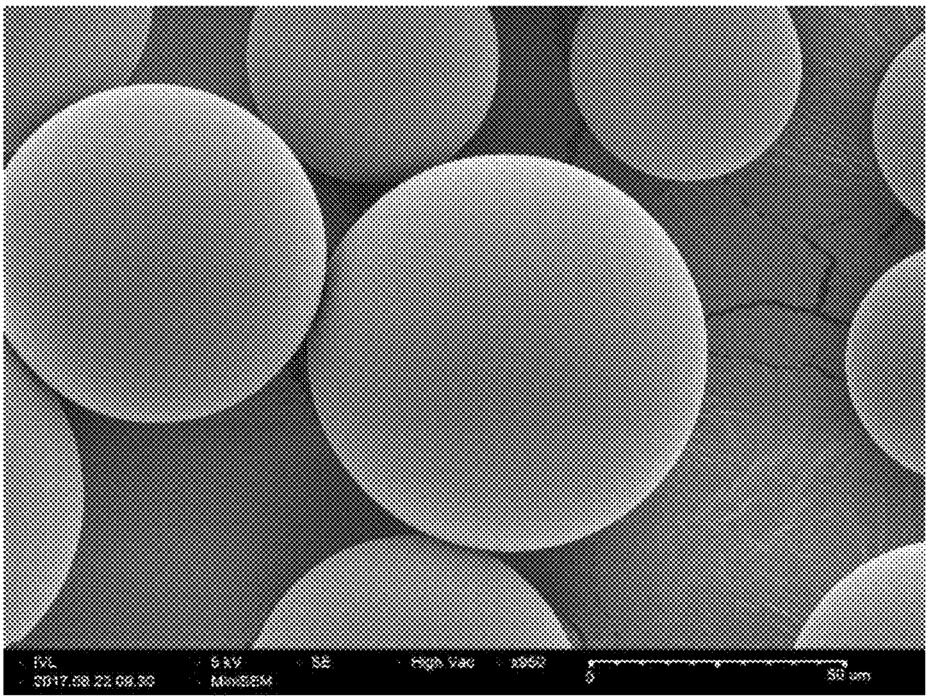
[FIG. 8]
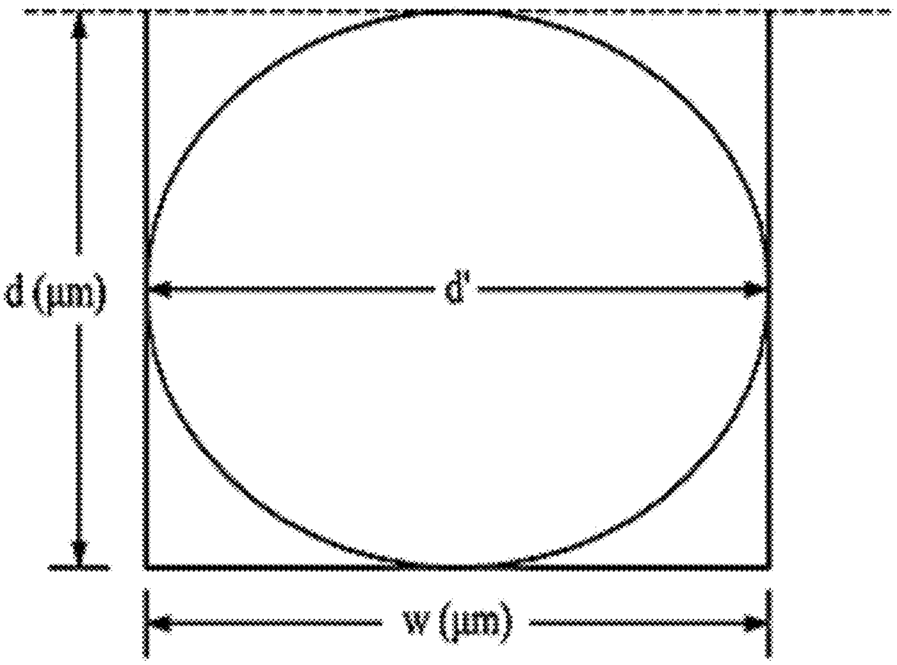

[FIG. 9]
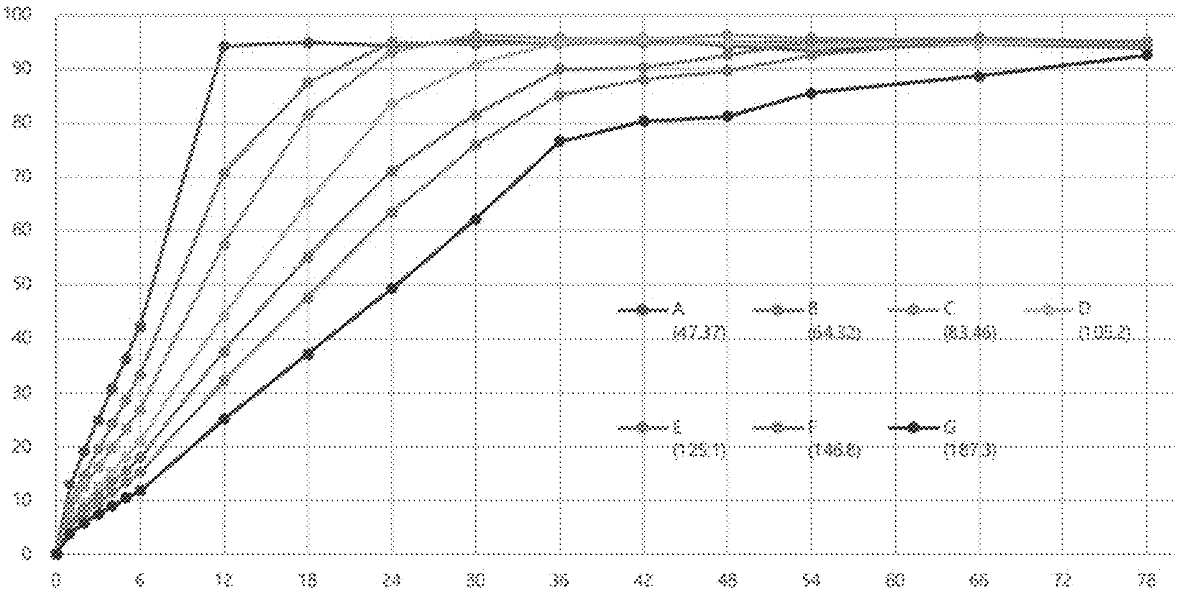
[FIG. 10]
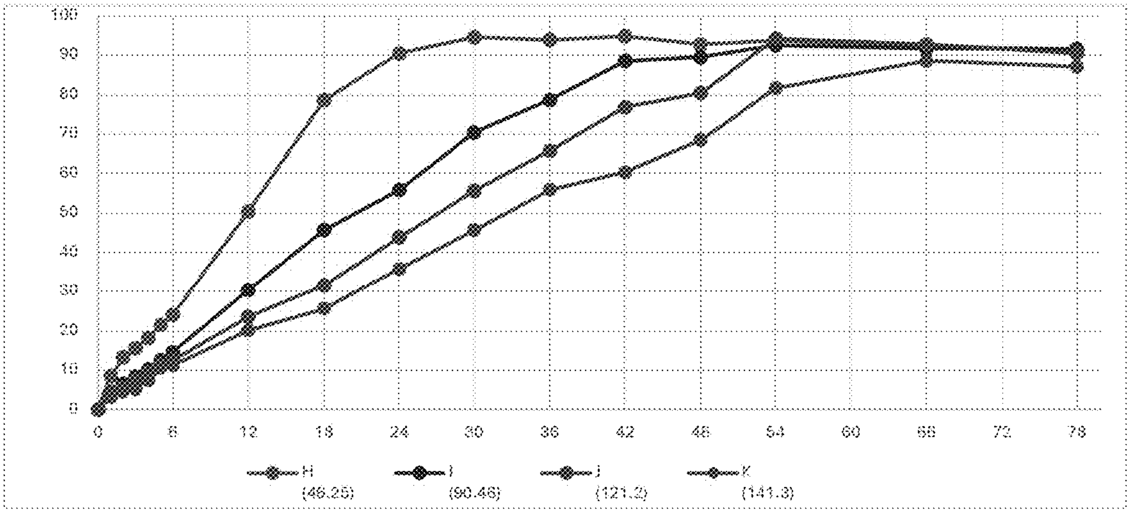

MICROPARTICLES CONTAINING MOXIDECTIN, AND PREPARATION METHOD THEREFOR

CROSS-REFERENCE TO RELATED APPLICATIONS

This application is a Continuation-In-Part of application Ser. No. 16/771,196, dated Jun. 9, 2020, which in turn claims the benefit of PCT/KR2018/010324, filed on Sep. 5, 2018, and Korean Applications No. 10-2017-0113669 filed on Sep. 6, 2017, and No. 10-2018-0031979, filed on Mar. 20, 2018. The entire disclosures of all these applications are hereby incorporated by reference.

TECHNICAL FIELD

The present invention relates to microparticles comprising moxidectin, and a preparation method therefor, and more particularly, to microparticles comprising moxidectin capable of preventing heartworm disease, and a biodegradable polymer, and a preparation method therefor.

BACKGROUND ART

Heartworm disease (HWD) is a parasite called *Dirofilaria immitis* that is transmitted by mosquitoes, and is infected by dogs, cats, and weasels. As can be seen from the name, heartworm disease is parasitic on the hearts of mammals.

Adult heartworms grow up to 30 cm and are mainly parasitic in the pulmonary artery and the right ventricle. Mature female and male heartworms produce very small larvae called microfilariae (L1). These larvae are parasitic in the blood of infected animals and infect other animals through mosquitoes. Two weeks after the L1 enters the body of a mosquito, the L1 will have an infection ability, and the larvae having the infection ability will be again transmitted to other animals through mosquitoes. Larvae infected to other animals go through several stages of growth and move to the pulmonary artery 3 to 4 months later. Such mature adult heartworms survive for 5 to 7 years on average, and female and male heartworms produce a number of larvae through reproduction.

At least 1 to 200 heartworms may be parasitic in the heart and pulmonary arteries of infected animals. Since infection results in thickening of the pulmonary artery and inflammation, the heart needs to do more work in order to avoid heartworm disease and send blood to the lungs. Further, inflammation also occurs in the lungs. When the number of infecting heartworms is small, there may be no special symptoms, but in general, animals infected with heartworm disease may show exercise avoidance, coughing, weight loss, and the like as initial symptoms. When the infection is severe, symptoms such as severe cough, dyspnea, and heart failure may appear. When an animal infected with heartworm disease shows these symptoms, a case where the animal dies from heart failure also occurs.

When diagnosis confirms infection with heartworm disease, an arsenamide (caparsolate) may kill adult heartworms, or treatment may be performed using melarsomine. However, all the aforementioned therapeutic agents have side effects that cause severe irritation at an injection site and damage the liver and the kidneys to some degree.

Therefore, it is economical and safe to prevent heartworm disease before infection with heartworm disease. Prevention is carried out 6 to 8 weeks after birth. Examples of preventive agents for heartworm disease include diethylcarbamazine (DEC) taken daily, or ivermectin, milbemycin, moxidectin, selamectin, and the like taken monthly. All the preventive agents are excellent in prevention effects when administered properly, but need to be taken daily or monthly, so that the animals may be exposed to a risk of infection even by skipping the administration several times by mistake.

Therefore, there is an urgent need for developing a preventive agent for heartworm disease in which administration convenience is improved by maintaining the efficacy for 3 months to 6 months due to the administration one time using moxidectin capable of preventing heartworm disease.

PRIOR ART DOCUMENT

[Patent Document]

(Patent Document 1) KR10-2006-0005472 A1

DISCLOSURE

Technical Problem

The present invention relates to microparticles comprising moxidectin, and a preparation method therefor.

An object of the present invention is to provide extended release microparticles capable of continuously maintaining a heartworm disease prevention effect for 3 months to 6 months when the microparticles comprising moxidectin are administered, unlike preventive agents for heartworm disease in the related art, which need to be administrated daily or monthly due to the short half-life, and a preparation method therefor.

Another object of the present invention is to maintain the effect of administering a drug administration effect for a long period of time such as 3 months to 6 months by using extended release particles comprising moxidectin, to maintain an effective drug concentration at a constant level by controlling the release of a drug from the microparticles as an average diameter of particles is prepared to a predetermined micrometer size, and to reduce a foreign body sensation and pain during administration of the drug by comprising microparticles with a uniform size during application through injection.

Technical Solution

To achieve the aforementioned objects, as a specific embodiment of the present invention, the present invention relates to microparticles comprising moxidectin and a biodegradable polymer, in which the microparticles have a shape in which the moxidectin drug is uniformly distributed in spherical biodegradable polymer microparticles, and the microparticles have a particle average diameter of 45 to 130 μm.

As a specific embodiment of the present invention, the microparticles of the present invention may include the biodegradable polymer and moxidectin at a weight ratio of 4:1 to 9:1.

As a specific embodiment of the present invention, the microparticles of the present invention may release moxidectin continuously for 3 months to 6 months.

As a specific embodiment of the present invention, the biodegradable polymer of the present invention is selected from the group consisting of polylactic acid, polylactide (PLA), poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide)(PLGA), but the biodegradable polymer is not limited to the example.

As a specific embodiment of the present invention, the microparticles of the present invention are prepared by using a microchannel, and a width (w) of the cross section of the channel is within a ratio range of 0.7 to 1.3 for an average diameter (d') of the microparticles.

As a specific embodiment of the present invention, the microparticles of the present invention are prepared by using a microchannel, and a height (d) of the cross section of the channel is within a ratio range of 0.7 to 1.3 for an average diameter (d') of the microparticles.

A specific embodiment of the present invention relates to a pharmaceutical composition for prevention and treatment of heartworm disease, comprising the microparticles according to the present invention.

As a specific embodiment of the present invention, the present invention relates to a method for preparing microparticles comprising moxidectin, the method comprising: 1) preparing a first mixture by dissolving a biodegradable polymer and moxidectin in an organic solvent; 2) preparing a second mixture by dissolving a surfactant in water; 3) infusing the first mixture in Step 1) into a microchannel in a straight-line direction and allowing the first mixture to flow; 4) preparing microparticles in which moxidectin is uniformly distributed in spherical biodegradable polymer particles by infusing the second mixture in Step 2) into a microchannel formed on both side surfaces or one side surface thereof and allowing the second mixture to flow such that the first mixture in Step 3) can form an intersection point with a microchannel flowing in a straight-line direction, and intersecting a flow of the first mixture in a straight-line direction with a flow of the second mixture; 5) collecting the microparticles produced at the intersection point in Step 4); 6) evaporating and removing an organic solvent present in the microparticles by stirring the microparticles collected in Step 5); and 7) washing and drying the microparticles in Step 6), in which the microparticles have an average particle diameter of 45 to 130 μm.

As a specific embodiment of the present invention, the first mixture in Step 1) of the present invention may include a biodegradable polymer in an amount of 15 to 60 wt %.

As a specific embodiment of the present invention, the first mixture in Step 1) of the present invention may include the biodegradable polymer and moxidectin at a weight ratio of 4:1 to 9:1.

As a specific embodiment of the present invention, the biodegradable polymer of the present invention is selected from the group consisting of polylactic acid, polylactide (PLA), poly(lactic-co-glycolic acid), poly(lactide-co-glycolide)(PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide)(PLGA), but the biodegradable polymer is not limited to the example.

As a specific embodiment of the present invention, the organic solvent in Step 1) of the present invention is one or more selected from the group consisting of dichloromethane, chloroform, chloroethane, dichloroethane, trichloroethane, and a mixture thereof.

As a specific embodiment of the present invention, the second mixture in Step 2) of the present invention may include a surfactant in an amount of 0.2 wt % to 0.3 wt %.

As a specific embodiment of the present invention, the surfactant in Step 2) of the present invention is one or more selected from the group consisting of a non-ionic surfactant, an anionic surfactant, a cationic surfactant, and a mixture thereof.

As a specific embodiment of the present invention, Step 3) of the present invention may infuse the first mixture into a microchannel in a straight-line direction under a pressure of 1,000 to 1,500 mbar.

As a specific embodiment of the present invention, Step 4) of the present invention may infuse the second mixture into a microchannel formed on both side surfaces or one side surface so as to form an intersection point with a microchannel through which the first mixture flows in a straight-line direction, and may infuse the second mixture under a pressure of 1,500 to 2,000 mbar.

As a specific embodiment of the present invention, Step 5) of the present invention may collect microparticles in a bath comprising a mixed solution comprising a surfactant in an amount of 0.2 wt % to 0.3 wt %.

As a specific embodiment of the present invention, Step 6) of the present invention may include: Step 6-1) firstly stirring the microparticles at a rate of 200 to 400 rpm at 15 to 20° C. for 1 to 2 hours: Step 6-2) secondly stirring the microparticles at a rate of 300 to 500 rpm at 20 to 30° C. for 1 to 2 hours after the first stirring, and Step 6-3) thirdly stirring the microparticles at a rate of 400 to 600 rpm at 40 to 50° C. for 3 to 5 hours after the second stirring.

As a specific embodiment of the present invention, the microchannels in Steps 3) and 4) of the present invention are formed on a surface of a wafer, and an average diameter of the microchannels is 60 to 150 μm, preferably 80 to 120 μm, and more preferably 100 μm, but is not limited to the example.

Advantageous Effects

The present invention relates to microparticles containing moxidectin and a preparation method therefor, and more particularly to extended release microparticles capable of continuously maintaining a heartworm disease prevention effect for 3 months to 6 months by administering microparticles comprising moxidectin, and a preparation method therefor.

Further, the present invention is prepared such that the average diameters of the particles have a predetermined micrometer size, and thus reduces a foreign body sensation and pain during administration into an animal through injection, thereby enabling administration through injection to be facilitated.

DESCRIPTION OF DRAWINGS

FIG. 1 is a flowchart of a method for preparing microparticles comprising moxidectin of the present invention.

FIG. 2 is a graph of results for the drug release period according to the weight ratio of a biodegradable polymer and moxidectin of the present invention.

FIG. 3 is a graph of results for the drug release period according to the weight ratio of a biodegradable polymer and moxidectin of the present invention.

FIG. 4 is an SEM photograph of microparticles by the preparation method according to an exemplary embodiment of the present invention.

FIG. 5 is an SEM photograph of microparticles by the preparation method according to an exemplary embodiment of the present invention.

FIG. 6 is an SEM photograph of microparticles by the preparation method according to an exemplary embodiment of the present invention.

FIG. 7 is an SEM photograph of microparticles by the preparation method according to an exemplary embodiment of the present invention.

FIG. 8 is a view on the relationship between an average diameter of microparticles and a cross-section of a microchannel.

FIG. 9 is the in vitro cumulative amount of moxidectin release percentage as a function of time (hrs.) recorded with different particle sizes when the polymer is PLGA.

FIG. 10 is the in vitro cumulative amount of moxidectin release percentage as a function of time (hrs.) recorded with different particle sizes when the polymer is PLA.

BEST MODE

The present invention relates to microparticles comprising moxidectin and a biodegradable polymer, wherein the microparticles comprising moxidectin have a shape allowing a moxidectin drug to be uniformly distributed in spherical biodegradable polymer, and the average particle diameter of the microparticles is 45-130 μm, depending on the type of polymer.

Hereinafter, examples of the present invention will be described in detail so that a person skilled in the art to which the present invention pertains can easily carry out the invention. However, the present invention can be implemented in various different forms and is not limited to the Examples described herein.

The moxidectin of the present invention is a compound represented by the following Formula 1, and means a material used as a preventive agent for heartworm disease of animals.

[Formula 1]

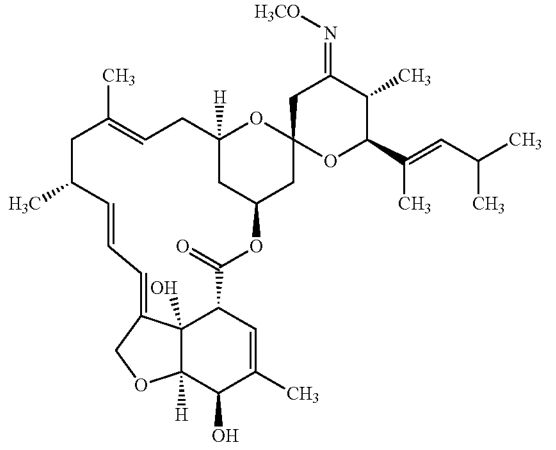

FIG. 1 is a flowchart of a method for preparing microparticles comprising moxidectin of the present invention.

According to the aforementioned flowchart, the preparation of the microparticles containing moxidectin of the present invention proceeds in the order of 1) preparing a first mixture (S100); 2) preparing a second mixture (S200); 3) infusing the first mixture into a microchannel in a straight-line direction (S300); 4) infusing the second mixture into a microchannel on both side surfaces or one side surface (S400); 5) collecting the microparticles (S500); stirring the collected microparticles (S600); and washing and drying the microparticles (S700).

More specifically, a method for preparing microparticles containing moxidectin according to an exemplary embodiment of the present invention will be described as follows.

Step 1) (S100) is a step of preparing a first mixture, specifically a step of preparing a first mixture by dissolving a biodegradable polymer and moxidectin in an organic solvent, in which the biodegradable polymer is selected from the group consisting of polylactic acid, polylactide (PLA), poly(lactic-co-glycolic acid), poly(lactide-co-glycolide)(PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide)(PLGA), but the biodegradable polymer is not limited to the example.

Further, the organic solvent is an organic solvent which is immiscible with water, is one or more selected from the group consisting of, for example, chloroform, chloroethane, dichloroethane, trichloroethane, and a mixture thereof, and is preferably dichloromethane, but the organic solvent is not limited to the example, and the organic solvent can dissolve a biodegradable polymer and moxidectin, and any organic solvent can be used as long as the organic solvent is not limited to the aforementioned example, and can be easily selected by a person with ordinary skill in the art.

Step 1) (S100) prepares a first mixture in which a biodegradable polymer and moxidectin are dissolved, and as the solvent, an organic solvent is used as described above. The moxidectin and the biodegradable polymer are completely dissolved by using an organic solvent using dissolution characteristics of moxidectin and the biodegradable polymer. After the moxidectin and the biodegradable polymer are completely dissolved, the first mixture contains the biodegradable polymer and moxidectin at a weight ratio of 4:1 to 9:1, preferably 4:1, but the weight ratio is not limited thereto. When the weight ratio of the biodegradable polymer and moxidectin is less than 4:1, that is, when the biodegradable polymer is contained at less than the above weight ratio, the weight ratio of the biodegradable polymer is smaller than the weight ratio of moxidectin, so that there occurs a problem in that it is difficult to prepare microparticles in a form that moxidectin is uniformly distributed and contained in the spherical biodegradable polymer particles, and when the weight ratio of the biodegradable polymer and moxidectin is more than 9:1, that is, when the biodegradable polymer is contained at more than the above weight ratio, the content of moxidectin in the microparticles is small, so that there occurs a problem in that the microparticles need to be administered in a large amount in order to administer the drug at a desired concentration.

More specifically, the biodegradable polymer is comprised in an amount of 15 to 60 wt %, preferably 15 wt % in the first mixture, but the amount is not limited to the example.

Step 2) (S200) is a step of preparing a second mixture, and prepares a second mixture by dissolving a surfactant in water. The surfactant can be used without limitation as long as the surfactant can help the biodegradable polymer solution form a stable emulsion. Specifically, the surfactant is one or more selected from the group consisting of a nonionic surfactant, an anionic surfactant, a cationic surfactant, and a mixture thereof, and more specifically, the surfactant is one or more selected from the group consisting of methyl cellulose, polyvinylpyrrolidone, lecithin, gelatin, polyvinyl alcohol, polyoxyethylene sorbitan fatty acid esters, polyoxyethylene castor oil derivatives, sodium lauryl sulfate, sodium stearate, esters, amines, linear diamines, fatty amines, and a mixture thereof, and is preferably polyvinyl alcohol, but the surfactant is not limited to the example.

Step 3) (S300) and Step 4) (S400) are steps of infusing the first mixture and the second mixture into a microchannel formed on a wafer and allowing the first mixture and the second mixture to flow.

More specifically, aluminum is deposited onto a silicon wafer by using an e-beam evaporator, and a photoresist is patterned on aluminum by using a photolithography technique. Thereafter, the wafer is aluminum-etched by using a photoresist as a mask, silicon is etched by deep ion reactive etching (DRIE) by using aluminum as a mask after removing the photoresist, and glass is anodically bonded onto the wafer and hermetically sealed after removing aluminum, thereby manufacturing the aforementioned microchannel.

Further, the microchannels have an average diameter of 60 to 150 μm, preferably 80 to 120 μm, and more preferably 100 μm, but the average diameter is not limited to the example.

In addition, a width (w) of the cross section and a height (d) of the cross section of the microchannel are closely associated with an average diameter (d') of microparticles to be prepared. As in FIG. 8, the width (w) of the cross section of the microchannel is within a ratio range of 0.7 to 1.3 for an average diameter (d') of the microparticles, and a height (d) of the cross section of the microchannel is within a ratio range of 0.7 to 1.3 for an average diameter (d') of the microparticles.

That is, when the average diameter (d') of the microparticles to be prepared is determined, it is possible to prepare microparticles with a desired size only when the width (w) and height (d) of the cross section of the microchannel are set to a ratio range of 0.7 to 1.3 for the d'.

Step 3) (S300) infuses the first mixture into a microchannel in a straight-line direction and allows the first mixture to flow, and Step 4) (S400) infuses the second mixture into a microchannel on both side surfaces or one side surface formed so as to form an intersection point with a microchannel in a straight-line direction, and allows the second mixture to flow.

That is, the first mixture flows along the microchannel in a straight-line direction, and the second mixture flows along the microchannel which forms an intersection point with the microchannel in a straight-line direction on both side surfaces or one side surface based on the microchannel in a straight-line direction, and meets the flow of the first mixture.

In this case, when the first mixture is infused into a microchannel in a straight-line direction, the first mixture is infused under a predetermined pressure condition and allowed to flow at a predetermined flow rate, and in this case, the pressure condition is 1,000 to 1,500 mbar, preferably 1,500 mbar, but is not limited to the example. Furthermore, when the second mixture is infused into a microchannel on both side surfaces or one surface, the second mixture is infused under a predetermined pressure condition and allowed to flow at a predetermined flow rate, and in this case, the pressure condition is 1,500 to 2,000 mbar, preferably 2,000 mbar, but is not limited to the example.

That is, in order to allow the second mixture forming an intersection point with the flow of the first mixture to flow at a faster flow rate than the first mixture to be infused into the microchannel in a straight-line direction, the second mixture is allowed to flow under a higher pressure condition.

As described above, the second mixture having a relatively faster flow rate compresses the first mixture at a point where the flow of the first mixture and the flow of the second mixture meet each other by varying the flow rates of the first mixture and the second mixture and making the flow rate of the second mixture faster than the flow rate of the first mixture, and in this case, due to repulsive force between the first mixture and the second mixture, the biodegradable polymer and moxidectin in the first mixture form spherical microparticles, and more specifically, microparticles in which moxidectin is uniformly distributed in the spherical biodegradable polymer are formed. Step 5) (S500) is a step of collecting microparticles, and prevents aggregation of initially produced microparticles by collecting the microparticles in a bath comprising the second mixture.

Step 5) (S500) uses the second mixture prepared in Step 2) (S200), that is, a mixed solution of a surfactant and water, and is used to prevent aggregation of collected microparticles by preparing the second mixture in Step 2) (S200), and then infusing a portion of the second mixture into a microchannel, and transferring the other portion to the bath in Step 5) (S500).

Step 6) (S600) is a step of stirring microparticles collected in the bath, and an organic solvent present on the surfaces of the microparticles is evaporated and removed by stirring the microparticles at a predetermined stirring rate under a predetermined temperature condition. In this case, the stirring condition proceeds in an order of firstly stirring the microparticles at a rate of 200 to 400 rpm at 15 to 20° C. for 1 to 2 hours; secondly stirring the microparticles at a rate of 300 to 500 rpm at 20 to 30° C. for 1 to 2 hours after the first stirring; and thirdly stirring the microparticles at a rate of 400 to 600 rpm at 40 to 50° C. for 3 to 5 hours after the second stirring.

For the stirring rate and temperature at which microparticles are stirred, the microparticles are stirred while slowly increasing each of the stirring rate and temperature according to the first, second, and third stirring periods, and as the temperature is increased step by step, the evaporation rate of the organic solvent present on the surfaces of the microparticles may be adjusted. That is, microparticles having smooth surfaces may be prepared by slowly evaporating the organic solvent present on the surfaces of the microparticles.

More specifically, in Step 6) (S600), the microparticles are firstly stirred at 15 to 20° C. for 1 to 2 hours, preferably at 17° C. for 1 hour. Thereafter, the microparticles are secondly stirred at 20 to 30° C. for 1 to 2 hours, preferably at 25° C. for 1 hour. Thereafter, the microparticles are thirdly stirred at 40 to 50° C. for 3 to 5 hours, preferably at 45° C. for 4 hours.

The temperature at which the first mixture and the second mixture flow in the microchannel is also 15 to 20° C., preferably 17° C. That is, after the mixtures flow in the microchannel and form an intersection point to produce microparticles, the temperature is constantly maintained at a low temperature of 15 to 20° C. until the collected microparticles are firstly stirred. Only when the low temperature is maintained during the process of preparing microparticles, it is possible to prepare and maintain spherical particles. That is, when the temperature is not under the low temperature condition, there occurs a problem in that it is difficult to prepare particles having a predetermined spherical shape.

Finally, Step 7) (S700) is a step of washing and drying the microparticles, and the microparticles from which the organic solvent on the surfaces is completely removed by stirring are washed several times with purified water which is sterilized and filtered to remove the surfactant remaining in the microparticles, and are later lyophilized.

The microparticles finally produced are in a form that the moxidectin drug is uniformly distributed in the spherical biodegradable polymer microparticles, have an average particle diameter of 45 to 130 μm, and contain the biodegradable polymer and moxidectin at a weight ratio of 4:1 to 9:1 The weight ratio of the biodegradable polymer and moxidectin included in the microparticles is the same as the weight ratio in the first mixture, and as the microparticles are prepared and the organic solvent is completely evaporated and removed, it is possible to prepare microparticles containing the biodegradable polymer and moxidectin at a ratio which is the same as the weight ratio in the first mixture.

Preparation Example: Preparation of Microparticles Comprising Moxidectin

Example 1

A first mixture was prepared by dissolving poly(lactide-co-glycolide) (PLGA) and moxidectin in dichloromethane. In this case, poly(lactide-co-glycolide) in the first mixture was contained in an amount of 15 wt %, and the weight ratio of poly(lactide-co-glycolide) and moxidectin was 9:1.

A second mixture comprising polyvinyl alcohol in an amount of 0.25 wt % was prepared by mixing a surfactant polyvinyl alcohol with water.

The first mixture and the second mixture were infused into a microchannel formed on a silicon wafer and allowed to flow. In this case, in order to allow the first mixture and the second mixture to flow at a predetermined flow rate, the first mixture and the second mixture were allowed to flow under a pressure condition of 1,000 mbar and under a pressure condition of 2,000 mbar, respectively. The temperature condition was maintained at 17° C.

Microparticles produced at an intersection point where the flow of the first mixture and the flow of the second mixture meet each other were collected in a bath comprising the second mixture. The microparticles collected in the bath were firstly stirred at a rate of 300 rpm at 17° C. for 1 hour, the temperature was increased to 20° C. and the microparticles were secondly stirred at a rate of 400 rpm for 1 hour, and then the temperature was increased to 45° C. and the microparticles were thirdly stirred at a rate of 500 rpm for 4 hours.

The microparticles completely stirred were washed several times with purified water which was sterilized and filtered, and were lyophilized, thereby preparing microparticles.

Example 2

Microparticles were prepared in the same manner as in Example 1, except that poly(lactide-co-glycolide) and moxidectin were comprised at a weight ratio of 4:1.

Example 3

Microparticles were prepared in the same manner as in Example 1, except that poly(lactide-co-glycolide) and moxidectin were comprised at a weight ratio of 2:1.

Example 4

Microparticles were prepared in the same manner as in Example 1, except that poly(lactide-co-glycolide) and moxidectin were comprised at a weight ratio of 12:1.

Examples 5 to 10

Microparticles were prepared in the same manner as in Example 1, but microparticles were collected in the bath comprising the second mixture, and then the stirring process was performed under the conditions in the following Table 1 as the stirring conditions.

TABLE 1

| | Stirring condition | Stirring temperature | Stirring time | Stirring rate |
|---|---|---|---|---|
| Example 5 | 1 | 15° C. | 1 hour | 300 rpm |
| | 2 | | 1 hour | 400 tpm |
| | 3 | | 4 hours | 500 rpm |
| Example 6 | 1 | 30° C. | 1 hour | 300 rpm |
| | 2 | | 1 hour | 400 rpm |
| | 3 | | 4 hours | 500 rpm |
| Example 7 | 1 | 45° C. | 1 hour | 300 rpm |
| | 2 | | 1 hour | 400 rpm |
| | 3 | | 4 hours | 500 rpm |
| Example 8 | 1 | 15° C. | 1 hour | 300 rpm |
| | 2 | 30° C. | 1 hour | |
| | 3 | 45° C. | 4 hours | |
| Example 9 | 1 | 15° C. | 1 hour | 400 rpm |
| | 2 | 30° C. | 1 hour | |
| | 3 | 45° C. | 4 hours | |
| Example 10 | 1 | 15° C. | 1 hour | 500 rpm |
| | 2 | 30° C. | 1 hour | |
| | 3 | 45° C. | 4 hours | |

Experimental Example 1: Drug Release Experiment of Microparticles Comprising Moxidectin 1. In-Vitro Drug Release Experiment About 100 mg of the microparticles in Examples 1 to 4 were put into a glass test container having a volume of 120 mL, and the container was filled with 100 mL of a release test solution. A drug release experiment was performed by putting the test container into a water bath at 45° C. and reciprocating the test container at an amplitude of 4 cm and a shaking frequency of 120 times/min as an experimental condition for acceleration of drug release. At the time of collecting the sample, the mixture was mixed by shaking the bottle well, and 1 mL of the sample was taken. After the sample was centrifuged at 13,000 rpm for 3 minutes, the supernatant was taken and analyzed with high performance liquid chromatography.

TABLE 2

| | Day | | | | | | | | | |
|---|---|---|---|---|---|---|---|---|---|---|
| | 1 | 2 | 3 | 4 | 7 | 10 | 14 | 16 | 21 | 25 |
| Example 3 | 28.1 | 42.5 | 57.2 | 69.3 | 92.5 | 94.2 | 94.3 | 95.1 | 95.1 | 96.3 |
| Example 2 | 12.7 | 22.3 | 34.2 | 43.8 | 66.8 | 88.2 | 94.5 | 94.3 | 94.5 | 95.0 |
| Example 1 | 6.5 | 12.3 | 20.1 | 28.1 | 50.2 | 72.0 | 86.2 | 93.1 | 93.5 | 96.2 |
| Example 4 | 2.2 | 7.3 | 12.1 | 18.6 | 35.7 | 56.3 | 72.5 | 78.6 | 88.3 | 93.9 |

(Unit %)

According to FIG. 2 and Table 2, in Examples 1 and 2, the moxidectin drug was released at a predetermined level until Day 25, so that effects of preventing or treating heartworm disease could be exhibited, whereas in Example 3, there are problems in that an excessive large amount of drug was released at the initial phase, the drug was almost completely released 7 days later, and accordingly, it is difficult to exhibit an effect of releasing the drug for a long period of time. In addition, in Example 4, there is a problem in that the amount of drug released at the initial stage was so small that the treatment effect of the moxidectin drug was minimal.

2. In-Vivo PK

By performing an experiment on the microparticles in Examples 1 and 2 in the same manner as in experiment 1, In-vitro PK data were analyzed, thereby confirming a continuous drug release effect until 3 months.

The results are shown in FIG. 3. As illustrated in FIG. 3, it can be confirmed that in Examples 1 and 2, moxidectin is released up to 3 months (90 days). Based on the corresponding results, it was confirmed that the microparticles of the present invention exhibited a continuous moxidectin release effect for 3 months.

Experimental Example 2: Study on Shapes of Microparticles

In order to study the shapes of microparticles according to the stirring conditions, the shapes of the microparticles prepared under the conditions in Examples 1 and 5 to 10 were studied through SEM photographs.

The results are shown in the following Table 3.

TABLE 3

| Experiment according to stirring condition | Preparation result of microparticles |
|---|---|
| Example 5 | Δ |
| Example 6 | Δ |
| Example 7 | Δ |

TABLE 3-continued

| Experiment according to stirring condition | Preparation result of microparticles |
|---|---|
| Example 8 | Δ |
| Example 9 | Δ |
| Example 10 | Δ |
| Example 1 | ○ |

A means that due to the effect of the remaining solvent, an aggregation phenomenon of microparticles occurs and the shapes of the microparticles are not uniform as in the SEM photographs in FIGS. 4 and 5. On the contrary, in Example 1, it was confirmed that the shapes of the microparticles were uniformly formed, and the aggregation phenomenon did not occur as in the SEM photographs in FIGS. 6 and 7.

Although preferred Examples of the present invention have been described in detail hereinabove, the right scope of the present invention is not limited thereto, and it should be understood that many variations and modifications of those skilled in the art using the basic concept of the present invention, which is defined in the following claims, will also fall within the right scope of the present invention.

[End Point of In Vitro Release According to Particle Size]

1. Poly(Lactide-Co-Glycolide) (PLGA)

Experimentation was conducted to compare the amount of moxidectin release percentage as a function of time for the following microparticles of different sizes: the microparticles comprising a biodegradable polymer (poly(lactic-co-glycolic acid), PLGA) and moxidectin at a weight ratio of 9:1, having an average particle diameter of 47.37 μm (Sample A), 64.32 μm (Sample B), 83.46 μm (Sample C), 105.2 μm (Sample D), 125.1 μm (Sample E), 146.8 μm (Sample F), and 187.3 μm (Sample G). The experimental conditions for all the microparticles were the same except for the average diameter.

Even with the same composition, there is a significant difference in the release period of a drug with a preventive effect. As evidence, FIG. 9 and Tables 4 and 5 are disclosed to compare the measured amount of drug release (%) of seven different size groups.

TABLE 4

Summary of in vitro and in vivo PK release as a function of duration.

| | In-vitro release time (hrs.) | | | | | | | | | | | | | | | | |
|---|---|---|---|---|---|---|---|---|---|---|---|---|---|---|---|---|---|
| | 0 | 1 | 2 | 3 | 4 | 5 | 6 | 12 | 18 | 24 | 30 | 36 | 42 | 48 | 54 | 66 | 78 |
| | In vivo PK (day) | | | | | | | | | | | | | | | | |
| | 0 | 3 | 6 | 9 | 12 | 15 | 18 | 36 | 54 | 72 | 90 | 108 | 136 | 154 | 162 | 198 | 234 |
| Sample A (47.37) | 0.00 | 12.96 | 19.18 | 25.06 | 30.73 | 36.32 | 42.26 | 94.23 | 94.85 | 94.21 | 95.45 | 94.56 | 95.65 | 94.21 | 93.45 | 94.65 | 93.89 |

TABLE 4-continued

Summary of in vitro and in vivo PK release as a function of duration.

| | In-vitro release time (hrs.) | | | | | | | | | | | | | | | | |
|---|---|---|---|---|---|---|---|---|---|---|---|---|---|---|---|---|---|
| | 0 | 1 | 2 | 3 | 4 | 5 | 6 | 12 | 18 | 24 | 30 | 36 | 42 | 48 | 54 | 66 | 78 |
| | In vivo PK (day) | | | | | | | | | | | | | | | | |
| | 0 | 3 | 6 | 9 | 12 | 15 | 18 | 36 | 54 | 72 | 90 | 108 | 136 | 154 | 162 | 198 | 234 |
| Sample B (64.32) | 0.00 | 9.43 | 14.69 | 19.61 | 24.19 | 28.72 | 33.49 | 70.73 | 87.44 | 95.06 | 94.56 | 95.03 | 94.78 | 94.87 | 95.02 | 95.06 | 94.07 |
| Sample C (83.46) | 0.00 | 8.20 | 12.45 | 16.25 | 19.80 | 23.32 | 26.99 | 57.42 | 81.60 | 93.15 | 96.35 | 95.63 | 95.41 | 96.25 | 95.63 | 95.24 | 95.12 |
| Sample D (105.2) | 0.00 | 6.15 | 9.44 | 12.47 | 15.33 | 18.10 | 20.99 | 44.33 | 65.25 | 83.58 | 90.89 | 94.85 | 95.77 | 94.78 | 94.32 | 94.68 | 95.08 |
| Sample E (125.1) | 0.00 | 5.79 | 8.52 | 11.09 | 13.38 | 15.64 | 17.98 | 37.64 | 55.17 | 71.11 | 81.59 | 89.88 | 90.25 | 92.56 | 95.14 | 95.65 | 94.65 |
| Sample F (146.8) | 0.00 | 4.96 | 7.30 | 9.49 | 11.46 | 13.38 | 15.36 | 32.21 | 47.62 | 63.34 | 75.96 | 85.09 | 88.01 | 89.65 | 92.54 | 95.63 | 95.03 |
| Sample G (187.3) | 0.00 | 3.97 | 5.81 | 7.46 | 8.96 | 10.43 | 11.84 | 25.10 | 37.25 | 49.35 | 62.01 | 76.62 | 80.34 | 81.20 | 85.60 | 88.65 | 92.56 |

The in vitro experimental conditions for all microparticles were as follows. The release test solution was prepared by dissolving 20 g of polysorbate 20 in 1 L of water and adding 0.08 g of sodium bicarbonate ($NaHCO_3$). The release test solution contains purified water 2% Tween 20. Microparticles (100 mg) were placed in an injection vial containing 100 mL of the release test solution, sealed, and then stirred and agitated at 55° C. at a water bath and 120 rpm to measure the difference in the amount of drug release.

TABLE 5

In-vivo PK duration estimations using PLGA.

| | Sample A 47.37 | Sample B 64.32 | Sample C 83.46 | Sample D 105.2 | Sample E 125.1 | Sample F 146.8 | Sample G 187.3 |
|---|---|---|---|---|---|---|---|
| D50 Accelerated release: at least 80% release point (hr.) | 12 | 24 | 30 | 36 | 54 | 66 | 78 |
| In-vivo PK drug retention time (day) | 36 | 72 | 90 | 108 | 162 | 198 | 234 |

In the in vivo animal experiments, moxidectin administered to beagle dogs was 0.2 mg/kg, and a total of 5 animals were subjected to subcutaneous injection to measure the concentration of moxidectin in the blood. The composition for subcutaneous injection was prepared by uniformly suspending the microparticles after adding 2.0 mL of a suspension solution based on one vial. The composition of the suspension solution is shown in Table 6.

TABLE 6

Composition of suspension solution.

| Content | Mixing purpose | Component | Amount (mg) |
|---|---|---|---|
| 2.0 mL | Isotonic agent | D-Mannitol | 100.0 |
| | Suspending agent | Sodium Carboxymethylcellulose | 10.0 |

TABLE 6-continued

Composition of suspension solution.

| Content | Mixing purpose | Component | Amount (mg) |
|---|---|---|---|
| | Suspending agent | Polysorbate 80 | 20.0 |
| | Solvent | Water for injection | Remainder |

As shown in FIG. 9 and Tables 4 and 5, the microparticles of 83.46, 105.2, and 125.1 μm released moxidectin for 90, 108, and 162 days when PLGA is employed in an actual animal experiment in vivo. By contrast, the microparticles of 47.37 and 64. 32 μm in average diameter released moxidectin for 12 and 24 hrs in vitro, respectively; therefore, the animal testing is expected to be released in about 36 and 72 days, respectively. The microparticles of 146.8 and 187.3 μm released moxidectin in 66 and 78 hrs in vitro; therefore, the expected period for animal testing is 198 and 234 days.

The experimentation shows that the microparticles of 80-130 μm continuously release moxidectin for 3-6 months, such that a heartworm disease prevention effect is effectively maintained until 3-6 months and completely release moxidectin before 6 months after administering the microparticles. These results prove the criticality of the average diameter of the microparticles. In other words, the diameter of 80-130 μm of the microparticles, as claimed, is critical to achieving the heartworm disease prevention effect for 3 to 6 months.

2. Polylactide (PLA)

PLA was used instead of PLGA to compare release rates according to size, and through this, in vivo PK duration was predicted. All experimental conditions were the same, and sample groups with different PLA sizes were tested as follows.

Sample H (average particle diameter: 46.25 μm)

Sample I (average particle diameter: 90.46 μm)

Sample J (average particle diameter: 121.2 μm)

Sample K (average particle diameter: 141.3 μm)

A second mixture was prepared by dissolving PLA and moxidectin in dichloromethane. In this case, the weight ratio of PLA and moxidectin was 9:1. All experimental conditions were the same as for PLGA.

Even with the same composition, there is a significant difference in the release period of a drug with a preventive effect. As evidence, FIG. 10 and Tables 7 and 8 are disclosed to compare the measured amount of drug release (%) of seven different size groups.

such that a heartworm disease prevention effect is effectively maintained until 3-6 months and completely release moxidectin before 6 months after administering the microparticles. These results also prove the criticality of the average diameter of the microparticles. In other words, the diameter of 45-120 μm of the microparticles, as claimed, is critical to achieving the heartworm disease prevention effect for 3 to 6 months.

INDUSTRIAL APPLICABILITY

The present invention relates to microparticles comprising moxidectin, and a preparation method therefor, and more particularly, to microparticles comprising moxidectin capable of preventing heartworm disease, and a biodegradable polymer, and a preparation method therefor.

The invention claimed is:

1. Microparticles comprising moxidectin and polylactide (PLA), wherein, the moxidectin is uniformly distributed in spherical PLA microparticles,

TABLE 7

Summary of in vitro and in vivo PK release as a function of duration (PLA).

| | 0 | 1 | 2 | 3 | 4 | 5 | 6 | 12 | 18 | 24 | 30 | 36 | 42 | 48 | 54 | 66 | 78 |
|---|---|---|---|---|---|---|---|---|---|---|---|---|---|---|---|---|---|
| H (46.25) | 0.00 | 8.65 | 13.25 | 15.56 | 18.26 | 21.53 | 23.95 | 50.45 | 78.65 | 90.46 | 94.56 | 93.89 | 94.85 | 92.75 | 93.78 | 92.14 | 91.54 |
| I (90.46) | 0.00 | 4.21 | 6.54 | 8.46 | 10.25 | 12.53 | 14.56 | 30.45 | 45.65 | 55.89 | 70.45 | 78.68 | 88.53 | 89.56 | 92.54 | 91.66 | 91.63 |
| J (121.2) | 0.00 | 4.56 | 5.48 | 7.73 | 9.56 | 11.53 | 12.54 | 23.56 | 31.58 | 43.85 | 55.65 | 65.84 | 76.87 | 80.45 | 94.21 | 92.78 | 90.54 |
| K (141.3) | 0.00 | 3.25 | 4.65 | 5.23 | 7.56 | 10.65 | 11.32 | 20.14 | 25.63 | 35.78 | 45.62 | 55.89 | 60.38 | 68.57 | 81.65 | 88.65 | 87.12 |

TABLE 8

In vivo PK duration estimations using PLGA (Samples A~G) and PLA (Samples H~K).

| | A | B | C | D | E | F | G | H | I | J | K |
|---|---|---|---|---|---|---|---|---|---|---|---|
| Average Diameter (pm) | 47.37 | 64.32 | 83.46 | 105.2 | 125.1 | 146.8 | 187.3 | 46.25 | 90.46 | 121.2 | 141.3 |
| Duration above 80% release (hr) | 12 | 24 | 30 | 36 | 54 | 66 | 78 | 30 | 54 | 54 | 66 |
| In-vivo PK drug retention duration (day) | 36 | 72 | 90 | 108 | 162 | 198 | 234 | 90 | 162 | 162 | 198 |

As shown in FIG. 10 and Tables 7 and 8, when the polymer is PLA, it was confirmed that the in vitro release duration of particles of the same size changed. In the case of PLA, microparticles with a size of 45 to 120 μm were observed to release drugs for 3 to 6 months.

The microparticles of 46.25, 90.46, and 121.2 μm released moxidectin for 90, 162, and 162 days when PLA is employed in an actual animal experiment in vivo. When the microparticles size is lower than 46.25 μm in average diameter, the animal testing is expected to be released in less than 90 days.

The experimentation shows that the microparticles of 45-120 μm continuously release moxidectin for 3-6 months, the microparticles have an average particle diameter of 45 to 120 μm, the PLA and the moxidectin are present at a weight ratio of 9:1, the microparticles reach at least 80% cumulative release of moxidectin in 30 to 54 hours, and the microparticles are configured to continuously release the moxidectin drug for 3 to 6 months after administering the microparticles.

2. The microparticles comprising moxidectin of claim 1, wherein the microparticles are prepared by using a microchannel, and a width (w) of a cross section of the channel is within a ratio range of 0.7 to 1.3 for an average diameter (d') of the microparticles.

3. The microparticles comprising moxidectin of claim 1, wherein the microparticles are prepared by using a microchannel, and a height (d) of a cross section of the channel is within a ratio range of 0.7 to 1.3 for an average diameter (d') of the microparticles.

4. A pharmaceutical composition for treatment of heartworm disease, comprising the microparticles according to claim 1.

* * * * *